United States Patent [19]

Ugo et al.

[11] Patent Number: 4,617,416
[45] Date of Patent: Oct. 14, 1986

[54] PROCESS FOR THE PREPARATION OF THIOCARBAMATES

[75] Inventors: Renato Ugo, Milan; Stefano Campolmi, Novara; Vittorio Carletti, Meda, all of Italy

[73] Assignee: Montedison S.p.A., Milan, Italy

[21] Appl. No.: 713,603

[22] Filed: Mar. 19, 1985

[30] Foreign Application Priority Data

Mar. 22, 1984 [IT] Italy ................. 20174 A/84

[51] Int. Cl.⁴ ......................................... C07C 155/02
[52] U.S. Cl. ................................. 558/242; 558/232; 558/243
[58] Field of Search .............. 260/455 A; 558/232, 558/241, 242

[56] References Cited

U.S. PATENT DOCUMENTS 4,222,938  9/1980  D'Amico ................. 260/455 A

OTHER PUBLICATIONS

Reid, Organic Chemistry of Bivalent Sulfur, vol. IV, p. 164, Chemical Publishing Co., Inc., 1962.
Dehmlow, et al., Phase Transfer Catalysis, Verlag Chemie, Deerfield Beach, Florida, 1980, p. 81.

Primary Examiner—Henry R. Jiles
Assistant Examiner—Robert C. Whittenbaugh

[57] ABSTRACT

There is disclosed a process for the preparation of thiocarbamates having the following general formula:

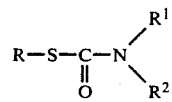

wherein:

R represents alkyl $C_1$–$C_4$ optionally substituted with one or more halogen atoms, alkenyl $C_2$–$C_4$ optionally substituted with one or more halogen atoms, phenyl optionally substituted with one or more halogen atoms, benzyl optionally substituted with one or more halogen atoms on the phenyl ring;

$R^1$ and $R^2$, equal or different from one another, represent alkyl $C_1$–$C_4$ or cycloalkyl;

consisting in reacting organic dithiocarbonates with organic carbamoyl halides, in the presence of an aqueous solution of an inorganic base and a phase transfer catalyst, at a temperature of 10° to 50° C. for time periods of 5 to 10 hours.

The thiocarbamates obtained are used as herbicides, fungicides, etc., and in general in various fields of "fine chemicals".

6 Claims, No Drawings

PROCESS FOR THE PREPARATION OF THIOCARBAMATES

BACKGROUND OF THE INVENTION

It is known that thiocarbamates constitute a wide class of industrial products used in different fields of "fine chemicals", particularly as herbicides and fungicides.

Among them mention can be made of Eptam, Pebulate, Cycloate, Butylate, Vernolate and Molinate manufactured by Stauffer, Drepamon by Montedison, Diallate and Triallate by Monsanto, Benthiocarb and Orbencarb by Kumiai, Methiobencarb by Bayer and Prothiocarb by Schering, all of which products have the following general formula:

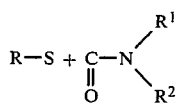

where, in each of said products, R, $R^1$ and $R^2$ have different meanings.

Due to the importance of this class of products, several processes for preparing them have been proposed.

Among them, the process known heretofore with widest industrial use involves the reaction between a mercaptide and a carbamoyl chloride, according to the scheme:

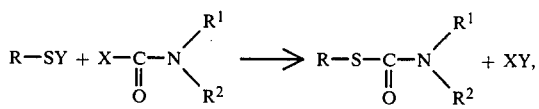

where: R, $R^1$, $R^2$ have different meanings, X is a halogen and Y is an alkaline metal.

The main disadvantage of this process lies in the use of mercaptans R-SH, which, as is known, are toxic, ill-smelling and volatile compounds.

THE PRESENT INVENTION

We have now found a new process simple and economical, for preparing, on an industrial scale, with high yields, thiocarbamates having formula:

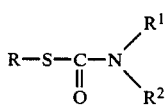

wherein:
R represents alkyl $C_1$-$C_4$ optionally substituted with one or more halogen atoms, alkenyl $C_2$-$C_4$ optionally substituted with one or more halogen atoms, phenyl optionally substituted with one or more halogen atoms, benzyl optionally substituted with one or more halogen atoms on the phenyl ring;
$R^1$ and $R^2$, equal or different from one another, represent alkyl $C_1$-$C_4$ or cycloalkyl.

The process is a general one and can be used for the preparation of any thiocarbamate included in the aforementioned formula, under substantially equivalent conditions.

The new process is characterized by the reaction of an organic thiocarbamate with a carbamoyl halide according to the equation:

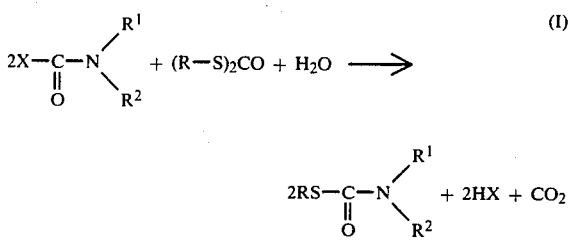

where R, $R^1$ and $R^2$ have the above stated meanings and X is Cl or Br.

Reaction (I) is preferably carried out in the presence of an aqueous alkaline base and of a catalyst for phase transfer, at a temperature ranging between 10° and 50° C., for time periods varying according to the products reacted, but in general between 5 and 10 total hours.

The initial products are reacted in the stoichiometric ratios required by the equation (I). When the reaction is over, the organic phase is found to be essentially formed by raw thiocarbamate, with possibly the catalyst if liposoluble. The thiocarbamate can be isolated either simply by decantation, if liquid, or by filtration, if solid, then it can be further purified, if necessary, according to conventional techniques.

In this way the process can be carried out in the absence of organic solvents.

The aqueous bases preferably used for effecting the reaction (I) are NaOH and 30% KOH. In this case the reaction course is represented by the following equation:

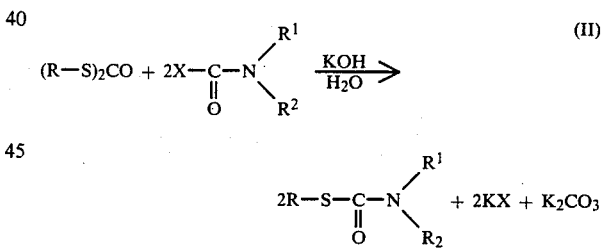

Commonly known catalysts of phase transfer can be used as suitable catalysts for carrying out the process according to the present invention, in particular "onium" salts with formula: $Q(R')_4Y$, where Q is an atom of N, P, As, Sb; R' represents an alkyl radical containing up to 20 C atoms; Y is a halogen selected from among Cl, Br and I. The preferred salts are ammonium salts, such as, for example, tricapryl-methyl-ammonium chloride (Aliquat 336) and phosphonium salts. Also crown ethers can be used as catalysts of phase transfer.

The use of thiocarbonates as initial product is extremely advantageous, in that they can be easily obtained through a sequence of reactions which can be carried out in succession with high yields and without intermediate purifications.

Their synthesis can be schematized as follows:

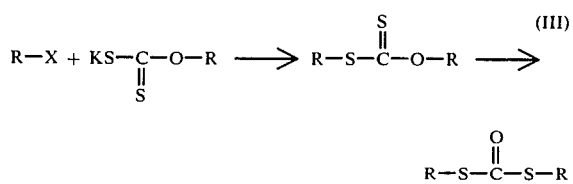

where X is halogen and R has the above-stated meanings.

Said process comprises two steps: the first one of preparation of O,S-dialkyldithiocarbonates from organic halide and potassium xanthogenates (the latter obtainable from carbonium sulfide, KOH and the corresponding alcohol), under conditions of phase transfer, and the second one of transposition of O,S-dialkyldithiocarbonates into S,S-dialkyl-dithiocarbonates, always through catalysis of phase transfer.

As both reactions forming the process (III) are catalyzed by the same onium salts, in practice they can be performed in sequence.

The preparation of dithiocarbonates to be used as starting products in the process (II), object of the present invention, according to the process (III), is also advantageous, in that process (II) and process (III), using the same catalysts, can be practically carried out in sequence in a single reactor. In this case, the xanthogenate/catalyst molar ratios are selected in the range 20:1 to 10:1, while the alkaline base/xanthogenate molar ratios are selected in the range 4:1 to 10:1.

The following example is provided for illustrating the invention in more detail and is not intended to be limiting.

EXAMPLE

Preparation of Potassium xanthogenate (A) 13.2 g of 85% KOH in lozenges and 100 cc of benzyl alcohol are placed in a 500 cc flask equipped with mechanical stirrer, thermometer, reflux condenser, dripping funnel, nitrogen inlet and bubble counter at outlet. Heating is carried out at 70°–80° C. for half an hour until all KOH has dissolved. Cooling is performed at approximately 25° C., then 15.2 g of carbonium sulfide are dripped in over a period of 15–20 minutes, keeping the temperature below 40° C. Stirring is continued for approximately 1 hour, then approximately 200 cc of ethyl ether are introduced, the precipitated product is filtered and dried. 43.8 g of potassium benzyl xanthogenate are obtained (yield=98.6%).

Preparation of S-benzyl di-sec-butylthiocarbamate (Drepamon)

(B) 2.44 g of potassium benzyl xanthogenate [0.011 moles of the product of (A)], 0.3 g approximately of Aliquat 336 (0.00007 moles), 1.26 g of benzyl chloride (0.01 moles) and 12 cc of water are placed in a 50 cc flask provided with magnetic stirrer, thermometer, nitrogen inlet. Stirring is continued at 25° C. for approximately 12 minutes, then at 40° C. for 2 hours. Cooling is then carried out and 6 g of 85% KOH in lozenges (0.09 moles) are introduced keeping the temperature at 25° C. 4.13 g of di-sec-butyl-carbamoyl chloride (0.022 moles) are finally added and the reaction is continued for 8–10 hours.

When the reaction is over, the organic phase is extracted with ethyl ether and gas chromatographically analyzed (n decane as internal standard). 4.78 g of S-benzyl di-sec-butyl-thiocarbamate (Drepamon) (0.017 moles) are found with 77.3% yield on the carbamoyl halide.

We claim:

1. A process for the preparation of thiocarbamates having general formula:

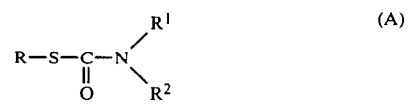

wherein:

R represents an alkyl $C_1$–$C_4$ optionally substituted with one or more halogen atoms, an alkenyl $C_2$–$C_4$ optionally substituted with one or more halogen atoms, a phenyl optionally substituted with one or more halogen atoms, a benzyl optionally substituted on the phenyl ring with one or more halogen atoms;

$R^1$ and $R^2$, equal or different from one another, represent an alkyl $C_1$–$C_4$; a cycloalkyl, according to the following reactions (I) and (II):

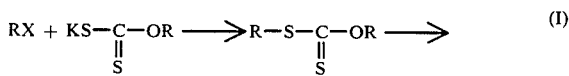

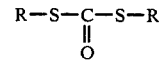

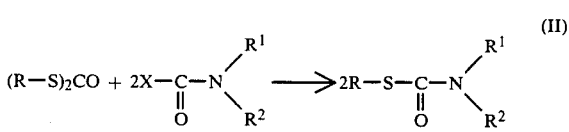

wherein X is a halogen; R, $R^1$ and $R^2$ have the same meanings as in general formula (A), reactions (I) and (II) being carried out in sequence without isolation of intermediate products, in alkaline aqueous-organic medium, in the presence of a phase transfer catalyst with xanthogenate/catalyst molar ratios of 20:1 to 10:1 and alkaline base/xanthogenate molar ratios of 4:1 to 10:1.

2. The process according to claim 1, wherein the organic dithiocarbonate and carbamoyl halide of reaction (II) are reacted in stoichiometric ratios (1:2), at a temperature between 10° and 50° C., for a time period ranging from 5 to 10 hours, in the presence of an aqueous solution selected from aqueous solutions of NaOH and KOH, and in the presence of a phase transfer catalyst.

3. The process according to claim 1, wherein the catalyst for phase transfer is an "onium" salt having formula $Q(R')_4Y$, where Q is an atom of N, P, As and Sb; R' represents an alkyl radical containing up to 20 C atoms; Y is a halogen selected from the group consisting of chlorine, bromine and iodine.

4. The process according to claim 3, wherein the "onium" salt is selected from the group consisting of tetrabutylammonium bromide, tricaprylmethylammonium chloride, trilaurylmethylammonium chloride, tetrabutylphosphonium chloride and tetrabutylphosphonium bromide.

5. The process according to claim 1, wherein the catalyst for phase transfer is a crown ether compound selected from the group consisting of dicyclohexyl-18-crown-6 and dibenzo-18-crown-6.

6. The process according to claim 1, wherein the thiocarbamate obtained is formed by S-benzyl di-sec-butyl-thiocarbamate.

* * * * *